United States Patent [19]

Grundmann et al.

[11] Patent Number: 5,202,419
[45] Date of Patent: Apr. 13, 1993

[54] ANTICOAGULATIVE PROTEIN PP4-X

[75] Inventors: Ulrich Grundmann, Lahntal-Grossfelden; Karl-Josef Abel; Egon Amann, both of Marburg, all of Fed. Rep. of Germany

[73] Assignee: Behringwerke Aktiengesellschaft, Marburg/Lahn, Fed. Rep. of Germany

[21] Appl. No.: 841,293

[22] Filed: Feb. 28, 1992

Related U.S. Application Data

[63] Continuation of Ser. No. 265,843, Nov. 1, 1988, abandoned.

[30] Foreign Application Priority Data

Nov. 30, 1987 [DE] Fed. Rep. of Germany ........ 3737237

[51] Int. Cl.$^5$ ............................................. C07K 13/00
[52] U.S. Cl. .................................... 530/350; 530/395; 530/851; 435/69.1; 435/69.2; 514/12; 930/250
[58] Field of Search ............... 530/395, 350, 851; 514/12; 435/69.1

[56] References Cited

U.S. PATENT DOCUMENTS

| | | | |
|---|---|---|---|
| 4,507,229 | 3/1985 | Bohn | 260/112 B |
| 4,732,891 | 3/1988 | Maki et al. | 514/21 |
| 4,937,324 | 4/1990 | Fujikawa et al. | 530/397 |

FOREIGN PATENT DOCUMENTS

| | | |
|---|---|---|
| 3315000 | 10/1984 | Fed. Rep. of Germany. |
| 04094 | 7/1986 | PCT Int'l Appl. . |
| 05659 | 8/1988 | PCT Int'l Appl. . |

OTHER PUBLICATIONS

Weber et al., "The Amino Acid Sequence of Protein II and its Phosphorylation Site for Protein Kinase C ... ", The EMBO Journal, 6:1599–1604, 1987.
Iwasaki et al., "Structure and Expression of cDNA for an Inhibitor of Blood Coagulation ... ", J. Biochem. 102:1261–1273 (1987).
Crumpton et al., "Protein Terminology Tangle", Nature, 345:212 (1990), and attached letters.
Iwasaki et al., "Structure and Expression of cDNA for Calphobindin II ... ", J. Biochemistry vol. 106, pp. 43–49, 1989.
F. Davidson et al., J. Biol. Chem. 262 (1987), pp. 1698–1705.
M. J. Geisow et al., Trends in Biol. Sc. II (1986), pp. 420–423.
Huang et al., Cell 46 (1986) pp. 191–199.
G. Cirino et al., Nature 328 (1987) pp. 270–272.
B. Wallner et al., Nature 320 (1986), pp. 77–81.
R. Lathe, J. Mol. Biol. 183 (1985), pp. 1–12.
Chirqwin et al., Biochemistry 18 (1979), pp. 5294–5299.
Aviv et al., Proc. Natl. Acad. Sci. USA 69 (1972), pp. 1408–1412.
Gubler et al., Gene 25 (1983), pp. 263–269.
T. Maniatis et al., Molecular Cloning. A Laboratory Manual, Cold Spring Harbor (1982), pp. 242–246.
Enquist et al., Methods in Enzymology 68 (1979), pp. 281–298.

*Primary Examiner*—Robert J. Hill, Jr.
*Assistant Examiner*—Nina Ossanna
*Attorney, Agent, or Firm*—Finnegan, Henderson, Farabow, Garrett and Dunner

[57] ABSTRACT

The protein PP4-X, whose amino acid sequence and the DNA sequence coding for this have been determined, has anticoagulative properties and can be prepared by genetic manipulation. PP4-X is used for therapeutic and diagnostic purposes.

4 Claims, 1 Drawing Sheet

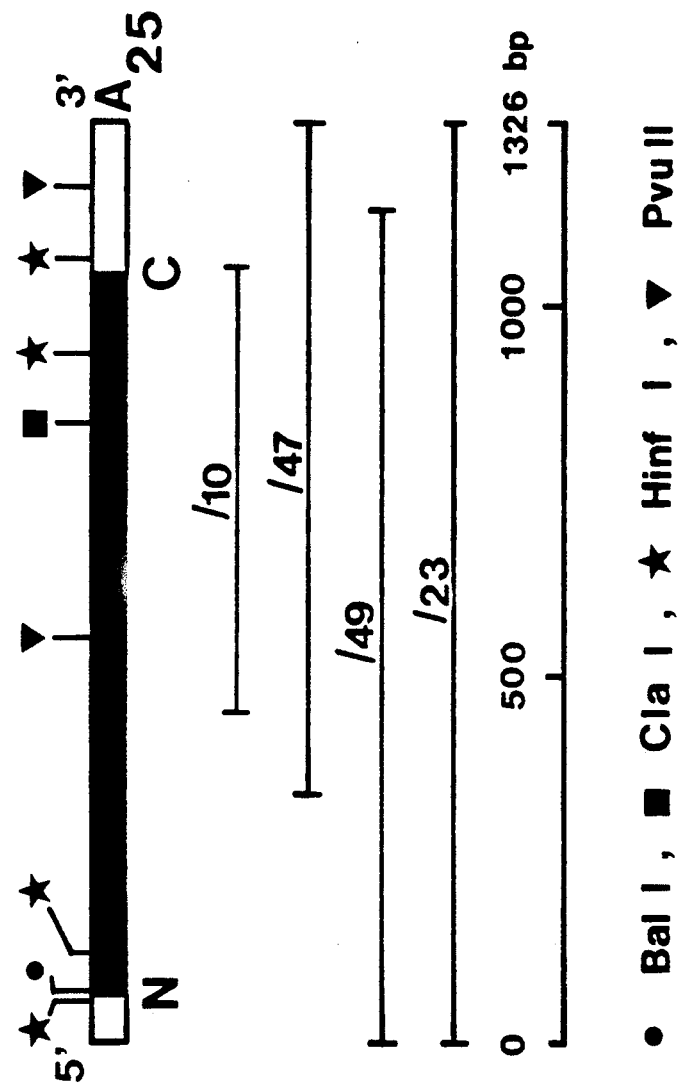

ANTICOAGULATIVE PROTEIN PP4-X

This application is a continuation of application Ser. No. 07/265,843, filed Nov. 1, 1988, now abandoned.

H. Bohn (German Offenlegungsschrift DE-A 3,315,000) was the first to describe the protein PP4 from human placentae and to characterize it by means of physicochemical parameters. Various oligonucleotides coding for PP4 peptides have now been used to search for the cDNA for PP4 in a placental cDNA bank. Surprisingly, a cDNA which codes for a protein which differs from PP4 has been found. Hence the protein resulting from the cDNA described herein is called PP4-X. The amino acid sequence, as well as the protein structure with 4 repeats, resembles that of the proteins lipocortin I and II.

PP4 oligopeptide A
MKGLGTDEES ILTLLTSRSN AQRQEISAAF KTLFGRDLLD D

PP4 oligopeptide B
MLVVLLQANRD PDAGIDEAQV EQDAQALFQA GELKXGTDEE KFI

The proteins lipocortin I and II or calpactin II and I have recently been disclosed as inhibitors of phospholipase A 2 (F. Davidson et al. (1987). J. Biol. Chem., 1698-1705; for review see: M. J. Geisow and J. H. Walker (1986), Trends in Biological Sciences 11, 420-423). Whereas lipocortin I acts as a substrate for EGF receptor tyrosine-protein kinase, lipocortin II is the human protein analogous to pp36, isolated from embryonal chicken fibroblasts or bovine intestinal epithelial cells, as principal substrate of pp60$^{src}$ kinase (K.-S. Huang et al. (1986) Cell 46, 191-199). Lipocortin II is, together with actin, a constituent of the internal membrane framework and external cytoskeleton. Lipocortin I has potent antiinflammatory properties, analogous to the corticosteroids, and it is presumed that the synthesis of these proteins is induced by corticosteroids (G. Cirino et al. (1987) Nature 328, 270-272). DNA sequence analyses and partial amino acid sequence analyses of the two proteins have led to both the nucleic acid sequences and the derived protein sequences being known (B. Wallner et al. (1986) Nature 320, 77-81 and K.-S. Huang et al., loc. cit.). The two sequences resemble one another greatly and, moreover, each has four repeat structures which contain a consensus sequence of about 20 amino acids. These four repeats in a single basic amino acid sequence are probably necessary for the membrane-binding properties—in the presence of Ca$^{2+}$—of the lipocortins.

Although we found PP4-X to have oligonucleotide sequences derived from PP4, it is not identical to PP4. This is based on the fact that just one oligonucleotide used for the search contains a base sequence which is relatively strongly conserved both in the repeats of lipocortin I and II and in those of PP4 and PP4-X.

PP4-X is an endogenous anticoagulant which occurs particularly in highly vascularized tissue such as the placenta, and in vessels. The anticoagulative properties make PP4-X suitable for use as an inhibitor in the coagulation cascade, since it reversibly inhibits blood coagulation at the thromboplastin stage. PP4-X binds via Ca ions to a negatively charged phospholipid surface, from which it can be released again with EDTA. A use resulting from this is in the prophylaxis of thrombosis, because PP4-X selectively, effectively and reversibly interrupts coagulation, without coagulation factors or inhibitors being respectively inactivated or activated by proteolysis. The coagulation potential is thus retained in full.

To obtain partial amino acid sequences and suitable oligonucleotide probes derived therefrom, the protein PP4 was broken down into cyanogen bromide fragments, two of which fragments (41 and 44 amino acids respectively) were sequenced. The following sequences were found:

On the basis of statistical data of R. Lathe (J. Mol. Biol. (1985) 183, 1-12), from the oligopeptide A was selected an oligonucleotide sequence having 35 bases.

(PP4 oligonucleotide 125)
ATGAAGGGCC TGGGCACAGA TGAGGAGAGC ATCCT and from oligopeptide B a sequence having 36 bases GATGCCCAGG CCCTGTTCCA GGCTGGCGAG CTGAAG
(PP4 oligonucleotide 104).

These oligonucleotide probes were used to screen a cDNA bank which had been prepared from mRNA from mature human placenta. The mRNA was first isolated from the placenta, and the cDNA was prepared therefrom. The latter was provided with EcoRI ends and ligated into the EcoRI cleavage site of the phage vector λgt10. 46 clones which had been identified using the abovementioned probes were analyzed further. Sequencing by methods known per se revealed the DNA sequence which codes for PP4-X.

BRIEF DESCRIPTION OF THE DRAWING

The FIGURE shows the restriction map of the cDNA sequence which encodes PP4-X. "N" designates the N terminus, "C" designates the C terminus of the coding region, and "A (25)" designates the poly-(A) sequence of 25 bases. The cDNA sequence represents the complete coding sequence of PP4-X.

Table 1 shows the DNA sequence (coding strand) which was found, and the amino acid sequence derived therefrom, of one clone (PP4-X/23). The complete cDNA has a length of 1326 base-pairs and an open reading frame of 972 base-pairs. The positions of the oligonucleotide probes 104 and 125 which hybridize between positions 599 and 634, and 851 and 885, respectively, are marked in Table 1.

TABLE 1

```
        10                    30                      50
CGCAGAGGAGGAGCGCAGCCGGCCTCGAAG AACTTCTGCTTGGGTGGCTGAACTCTGATC 70                    90                     110
TTGACCTAGAGTCATGGCCATGGCAACCAAAGGAGGTACTGTCAAAGCTGCTTCAGGATT
                M   A   M   A   T   K   G   G   T   V   K   A   A   S   G   F
```

TABLE 1-continued

```
                130                    150                       170
CAATGCCATGGAAGATGCCCAGACCCTGAGGAAGGCCATGAAAGGGCTCGGCACCGATGA
 N   A  M  E  D  A  Q  T  L  R  K  A  M  K  G  L  G  T  D  E 190                    210                       230
AGACGCCATTATTAGCGTCCTTGCCTACCG CAACACCGCCCAGCGCCAGGAGATCAGGAC
 D   A  I  I  S  V  L  A  Y  R  N  T  A  Q  R  Q  E  I  R  T 250                    270                       290
AGCCTACAAGAGCACCATCGGCAGGGACTTGATAGACGACCTGAAGTCAGAACTGAGTGG
 A   Y  K  S  T  I  G  R  D  L  I  D  D  L  K  S  E  L  S  G 310                    330                       350
CAACTTCGAGCAGGTGATTGTGGGGATGATGACGCCCACGGTGCTGTATGACGTGCAAGA
 N   F  E  Q  V  I  V  G  M  M  T  P  T  V  L  Y  D  V  Q  E 370                    390                       410
GCTGCAAAGGGCCATGAAGGGAGCCGGCACTGATGAGGGCTGCCTAATTGAGATCCTGGC
 L   Q  R  A  M  K  G  A  G  T  D  E  G  C  L  I  E  I  L  A 430                    450                       470
CTCCCGGACCCCTGAGGAGATCCGGCGCATAAGCCAAACCTACCAGCAGCAATATGGACG
 S   R  T  P  E  E  I  R  R  I  S  Q  T  Y  Q  Q  Q  Y  G  R 490                    510                       530
GAGCCTTGAAGATGACATTCGCTCTGACACATCGTTCATGTTCCAGCGAGTGCTGGTGTC
 S   L  E  D  D  I  R  S  D  T  S  F  M  F  Q  R  V  L  V  S 550                    570                       590
TCTGTCAGCTGGTGGGAGGGATGAAGGAAATTATCTGGACGATGCTCTCGTGAGACAGGA
 L   S  A  G  G  R  D  E  G  N  Y  L  D  D  A  L  V  R  Q  D 610                    630                       650
TGCCCAGGACCTGTATGAGGCTGGAGAGAAGAAATGGGGGACAGATGAGGTGAAATTTCT
 A   Q  D  L  Y  E  A  G  E  K  K  W  G  T  D  E  V  K  F  L 670                    690                       710
AACTGTTCTCTGTTCCCGGAACCGAAATCACCTGTTGCATGTGTTTGATGAATACAAAAG
 T   V  L  C  S  R  N  R  N  H  L  L  H  V  F  D  E  Y  K  R 730                    750                       770
GATATCACAGAAGGATATTGAACAGAGTATTAAATCTGAAACATCTGGTAGCTTTGAAGA
 I   S  Q  K  D  I  E  Q  S  I  K  S  E  T  S  G  S  F  E  D 790                    810                       830
TGCTCTGCTGGCTATAGTAAAGTGCATGAG GAACAAATCTGCATATTTTGCTGAAAAGCT
 A   L  L  A  I  V  K  C  M  R  N  K  S  A  Y  F  A  E  K  L 850                    870                       890
CTATAAATCGATGAAGGGCTTGGGCACCGATGATAACACCCTCATCAGAGTGATGGTTTC
 Y   K  S  M  K  G  L  G  T  D  D  N  T  L  I  R  V  M  V  S 910                    930                       950
TCGAGCAGAAATTGACATGTTGGATATCCG GGCACACTTCAAGAGACTCTATGGAAAGTC
 R   A  E  I  D  M  L  D  I  R  A  H  F  K  R  L  Y  G  K  S 970                    990                       1010
TCTGTACTCGTTCATCAAGGGTGACACATCTGGAGACTACAGGAAAGTACTGCTTGTTCT
 L   Y  S  F  I  K  G  D  T  S  G  D  Y  R  K  V  L  L  V  L 1030                   1050                      1070
CTGTGGAGGAGATGATTAAAATAAAAATCCCAGAAGGACAGGAGGATTCTCAACACTTTG
 C   G  G  D  D 1090                   1110                      1130
AATTTTTTTAACTTCATTTTTCTACACTGCTATTATCATTATCTCAGAATGCTTATTTCC 1150                   1170                      1190
AATTAAAACGCCTACAGCTGCCTCCTAGAATATAGACTGTCTGTATTATTATTCACCTAT 1210                   1230                      1250
AATTAGTCATTATGATGCTTTAAAGCTGTACTTGCATTTCAAAGCTTATAAGATATAAAT 1270                   1290                      1310
GGAGATTTTAAAGTAGAAATAAATATGTATTCCATGTTTTTAAAAAAAAAAAAAAAAAAA
AAAAAA
```

It is possible according to the invention for the coding cDNA to be used, with the aid of suitable expression systems, to express PP4-X. Furthermore, the type of modification of PP4-X can be influenced by the choice of the host. Thus, no glycosylation takes place in bacteria, whereas that taking place in yeast cells differs from that in higher eukaryotic cells.

Knowing the amino acid sequence of PP4-X, it is possible to prepare, by conventional or genetic manipulation methods, amino acid part-sequences which can be used as antigens for the preparation of polyclonal or monoclonal antibodies. Such antibodies can be used not only for diagnostic purposes but also for the preparation of antibody columns with which it is possible to separate PP4-X from solutions which contain it together with other proteins.

It is also possible using the cDNA, or parts thereof, to isolate in a straightforward manner from a genomic bank the genomic clone which codes for PP4-X and which not only facilitates the expression in eukaryotic cells but also allows further diagnostic conclusions to be drawn.

The invention is further defined in the patent claims and is explained in detail in the examples which follow.

The following abbreviations are used, apart from those explained in the text:
EDTA = sodium ethylenediaminetetraacetate
SDS = sodium dodecyl sulfate
DTT = dithiothreitol
BSA = bovine serum albumin

EXAMPLES

1. Isolation of RNA from human placenta

RNA was obtained from mature human placenta (method of Chirgwin et al., Biochemistry 18 (1979) 5294-5299). About 10 g of placental tissue were ground in liquid nitrogen in a mortar, suspended in 80 ml of 4M guanidinium thiocyanate containing 0.1M mercaptoethanol, and treated in a homogenizer (Ultraturrax) at 20.000 rpm for 90 sec. The lysate was centrifuged (Sorvall GSA rotor) at 7.000 rpm for 15 min. and the supernatant was precipitated with 2 ml of 1M acetic acid and 60 ml of abs. ethanol at $-20°$ C. overnight. The nucleic acids were sedimented at 6.000 rpm and $-10°$ C. for 10 min and then completely dissolved in 40 ml of 7.5M guanidinium hydrochloride (pH 7.0) and precipitated with a mixture of 1 ml of 1M acetic acid and 20 ml of abs. ethanol. To remove the DNA, the precipitation was repeated once more with each of the volumes being halved. The RNA was dissolved in 12 ml of $H_2O$, precipitated with a mixture of 1.2 ml of 4M potassium acetate and 24 ml of abs. ethanol, sedimented and, finally, again taken up in 10 ml of $H_2O$ (1 ml per g of tissue).

2. Obtaining poly(A)-containing placental mRNA

To obtain poly(A)-containing mRNA, the placental RNA was fractionated by oligo(dT)-cellulose chromatography (Aviv and Leder, Proc. Natl. Acad. Sci. USA 69 (1973) 1408-1412) in 2 ml Pasteur pipettes in LiCl. About 5 mg of placental RNA in buffer 1 (500 mM LiCl, 20 mM Tris (pH 7.5), 1 mM EDTA, 0.1% SDS) were applied to the column. Whereas the poly(A)+ RNA was bound to oligo(dT)-cellulose, it was possible to elute the poly(A)− RNA again. After a washing step with buffer 2 (100 mM LiCl, 29 mM Tris (pH 7.5), 1 mM EDTA, 0.1% SDS), the poly(A)+RNA (placental mRNA) was eluted from the column with buffer 3 (5 mM Tris (pH 7.5), 1 mM EDTA, 0.05% SDS).

For further purification, the poly(A)+RNA was adjusted to buffer 1 and again chromatographed on oligo(dT)cellulose. The yield of placental poly(A)+RNA after this second purification step was about 4% of the RNA used.

3. Synthesis of cDNA from human placenta (placental cDNA) and double-stranded cDNA (dsDNA)

The integrity of the poly(A)-containing placental mRNA was checked in a 1.5% agarose gel before the cDNA synthesis.

Then 4 μg of placental mRNA were dissolved in 65.5 μl of $H_2O$, denatured at 70° C. for 10 min and cooled again in ice. The cDNA was synthesized in a 100 μl mixture after addition of 20 μl of $RT_1$ buffer (250 mM Tris (pH 8.2) at 42° C., 250 mM KCl, 30 mM $MgCl_2$), 2.5 μl of 20 mM dNTP (i.e. all four deoxynucleoside triphosphates), 1 μl of oligo(dT) of 1 μg/ml, 1 μl of 1M DTT, 2 μl of RNAsin and 8 μl of reverse transcriptase (24 U/μl) at 42° C. for 90 min. Double-stranded cDNA (dsDNA) was synthesized by the method of Gubler and Hoffmann (Gene 25 (1983) 263-269). The synthesis was carried out immediately after the cDNA synthesis by addition of 305.5 μl of $H_2O$, 80 μl of $RT_2$ buffer (100 mM Tris (pH 7.5), 25 mM $MgCl_2$, 500 mM KCl, 50 mM DTT, 250 μg/ml BSA), 2 μl of RNase H (2 U/μl), 2.5 μl of *E. coli* DNA ligase (5 U/μl), 5 μl of 15 mM β-NAD, and 5 μl of DNA polymerase I (5 U/μl) and incubation at 15° C. for 5 h. The reaction was stopped by heat-inactivation (70° C., 30 min).

After addition of 55 μl of 250 μM dNTP, 55 μl of 10 mM Tris (pH 7.5), 10 mM $MgCl_2$, 10 μg/ml BSA, 3 μl of T4 DNA polymerase I (1 U/μl), 2 μl of RNase H (2 U/μl) and 2 μl of RNase A (2 μg/ml) to the reaction mixture it was incubated at 37° C. for a further 13 min in order to ensure that the synthesis on the second DNA strand was complete ("repair reaction").

4. Ligation of EcoRI linkers to the dsDNA, and opening of the linkers

To set up a placental cDNA bank, the dsDNA was provided with EcoRI ends in order to be able to ligate it into the EcoRI cleavage site of the phage vector λgt10 (T. Maniatis et al. (1982), Molecular Cloning, A Laboratory Manual, Cold Spring Harbor). For this purpose, the DNA was
a) treated with EcoRI methylase in order to protect internal EcoRI cleavage sites of the dsDNA, and
b) provided with EcoRI linkers which
c) were then opened with EcoRI.

Re a):
The methylase reaction of dsDNA was carried out directly following the repair reaction after addition of 25 μl of 500 mM EDTA (pH 8.0), 60 μl of methylase buffer (100 mM NaOAc (pH 5.2), 2 mg of S-adenosyl-L-methionine) and 2 μl of EcoRI methylase (20 U/μl) by incubation at 37° C. for 30 min. The reaction mixture was extracted with phenol, and the dsDNA was precipitated with 60 μl of 4M NaOAc and 1300 μl of ethanol. The dsDNA was washed twice with 70% ethanol, extracted by shaking once with ether, and dried.

Re b):
The EcoRI-methylated dsDNA was dissolved in 88 μl of $H_2O$ and, after addition of 10 μl of ligase buffer (500 mM Tris (pH 7.4), 100 mM $MgCl_2$, 100 mM DTT, 100 mM spermidine, 10 mM ATP, 1 mg/ml BSA) and 1 μl of T4 DNA ligase (10 U/μl), was ligated with 1 μl of EcoRI linkers (0.5 μg/μl) (pGG-AATTCC and pA-GAATTCT) at 15° C. overnight.

Re c):

The volume of the ligase mixture was made up to 120 μl with 6 μl of H₂O, 12 μl of 10×EcoRI buffer and 2 μl of EcoRI (120 U/μl). The EcoRI digestion was carried out at 37° C. for 2 h.

5. Removal of unbound linkers on a potassium acetate gradient, and selection of the dsDNA for size All unbound EcoRI linkers were removed from the dsDNA by applying the EcoRI reaction mixture in toto to a potassium acetate gradient (5–20% KOAc, 1 mM EDTA, 1 μl/ml ethidium bromide) and centrifuging (Beckman SW 65 rotor) at 50,000 rpm and 20° C. for 3 h.

The gradient was fractionated from below in such a way that the first five fractions measured 500 μl, and all the remainder measured 100 μl. The fractions were precipitated with 0.01 volume of acrylamide (2 mg/ml) and 2.5 volumes of ethanol, washed once with 70% strength ethanol and dried, and each was taken up in 5 μl of H₂O.

To determine the size of the dsDNA, 1 μl of each fraction was analyzed in 1.5% agarose gel. In addition, the quantity of dsDNA was determined using 1 μl of each fraction.

Fractions containing dsDNA above 1000 bp were combined, and the sample was concentrated until the final concentration was 27 μg/ml.

6. Insertion of the dsDNA into the phage vector λgt10, and in vitro packaging reaction The dsDNA was inserted into the EcoRI cleavage site of the phage vector λgt10 (Vector Cloning Systems, San Diego, Cal.) in a 4 μl ligase mixtures: 2 μl of dsDNA, 1 μl of λgt10×EcoRI (1 μg/ml), 0.4 μl of ligase buffer, 0.5 μl of H₂O, 0.1 μl of T4 DNA ligase. The mixture was incubated at 15° C. for 4 h.

To establish the placental cDNA bank in the phage vector λgt10, the ligase mixture was subsequently subjected to an in vitro packaging reaction with the λ-lysogenic cell extracts $E.$ $coli$ NS 428 and NS 433 at room temperature for 2 h (Vector Cloning Systems, San Diego, Cal.; Enquist and Sternberg, Methods in Enzymology 68, (1979), 281–298). The reaction was stopped with 500 μl of suspending medium (SM: 0.1M NaCl, 8 mM MgSO₄, 50 mM Tris (pH 7.5), 0.01% gelatine), and 2 drops of chloroform.

7. Titer determination and analysis of the placental cDNA bank

The number of plaque-forming units (PFU) of the placental cDNA bank were determined using competent cells of $E.$ $coli$ K 12 strain C600 HFL: it was 1×10⁶ PFU. About 80% of all the phages contained DNA inserts larger than 1000 base-pairs.

8. Oligonucleotide probes for screening the placental cDNA bank

Two oligonucleotide probes were synthesized for the analysis of the placental cDNA bank. Their sequences were derived from the amino acid sequence of several cyanogen bromide fragments of the anticoagulative protein PP4-X.

The manner of construction and the use of the two probes essentially followed the rules of R. Lathe, loc. cit.

Both oligonucleotide sequences were labeled at the 5' end using T4 polynucleotide kinase in the presence of (γ-³²P) ATP (about 1 μg of DNA (γ-³²P) ATP:3000 Ci/mmol, 10 μCi/μl, with 6 μl/40 ul of reaction mixture being used). The probes had a specific activity of 1×10⁸ Bq/μl or 1.5×10⁶ Bq/pmol.

9. Screening of the placental cDNA with PP4-specific oligonucleotides

1×10⁶ PFU of the placental cDNA bank were examined with the PP4 oligonucleotide probes 104 and 125 together. For this purpose, 3×10⁴ PFU were plated out with cells of the $E.$ $coli$ K 12 strain C 600 HFL in soft agar on 13.5 cm Petri dishes and incubated at 37° C. for 6 h. Lysis was still incomplete at this time. The plates were incubated in a refrigerator overnight, and the phages were transferred to nitrocellulose filters (Schleicher & Schüll, BA 85, Ref.-No. 401124) (duplicates). The nitrocellulose filters and Petri dishes were marked with an injection needle to allow assignment later. During the processing of the nitrocellulose filters, the Petri dishes were stored in a cold room. The DNA on the nitrocellulose filters was denatured by placing the filters on filter paper (Whatman M3) impregnated with 1.5M NaCl, 0.5M NaOH for 5 min. The filters were then renatured in the same way using 1.5M NaCl, 0.5M Tris (pH 8.0) and washed with 2×SSPE (0.36M NaCl, 16 mM NaOH, 20 mM NaH₂PO₄, 2 mM EDTA). The filters were then dried in vacuo at 80° C. for 2 h. The filters were washed in 3×SSC, 0.1% SDS (20×SSC=3M NaCl, 0.3M Na citrate) at 65° C. for 4 h and prehybridized at 65° C. for 4 h (prehybridization solution: 0.6M NaCl, 0.06M Tris (pH 8.3), 6 mM EDTA, 0.2% non-ionic synthetic sucrose polymer (ᴿFicoll), 0.2% polyvinylpyrrolidone 40, 0.2% BSA, 0.1% SDS, 50 μg/ml denatured herring sperm DNA). The filters were incubated overnight with the addition of 100,000–200,000 Bq of the labeled oligonucleotide per ml of hybridization solution (as prehybridization solution but without herring sperm DNA) in beakers or in sealed polyethylene films, shaking gently. The hybridization temperature was 44° C. The nitrocellulose filters were washed with 6×SSC, 0.05M sodium pyrophosphate at room temperature for one hour and at the relevant hybridization temperature for a further hour. The filters were dried and autoradiographed overnight. Signals which appeared on both duplicates of the X-ray film were assigned to the Petri dish, and the region (about 50 plaques) was punched out with the wide end of a Pasteur pipette, and the phages were resuspended in 1 ml of SM buffer. Positive phages were singled out over three cycles until a single clone was obtained.

In total, 1×10⁶ PFU of the placental cDNA bank were examined. 54 signals were identified on duplicate filters. On further screening with the individual probes, it emerged that nine clones reacted with both probes. All these nine clones carry a PP4-X coding sequence, with a maximum length of 1326 base-pairs for the clone PP4-X/23. Sequence analysis of the PP4-X clones subsequently showed that eight mismatches with the PP4-X sequence which has been found occur over the complete length of each of the two probes (Table 2).

TABLE 2

PP4-X seq. versus PP4 oligonucleotide 104

TABLE 2-continued

```
596 CAGGATGCCCAGGACCTGTATGAGGCTGGAGAGAAGAAATGGGGGACAGA 645
    |||||||||| ||||| ||||||| ||| |||
1..    GATGCCCAGGCCCTGTTCCAGGCTGGCGAGCTGAAG              36
```

PP4-X seq. versus PP4 oligonucleotide 125

```
846 AATCGATGAAGGGCTTGGGCACCGATGATAACACCCTCATCAGAGTGATG 895
    |||||||| ||||||| ||||| | | ||| |
1...     ATGAAGGGCCTGGGCACAGATGAGGAGAGCATCCT             35
```

10. DNA sequence analysis

The phage clones PP4-X/10, /23, /47 and /49 were propagated, and the DNA of each of them was extracted. In each case the EcoRI fragment was isolated and ligated into the EcoRI sites of the vector pIC19H for restriction analyses and of the vector M13mp8 for sequence analyses using the enzymatic dideoxy method of Sanger. The sequence shows an open reading frame and codes for a protein having a maximum of 321 amino acids (Tab. 1).

11. Expression of PP4-X in E. coli a) Expression of the mature unfused PP4-X protein The expression vector pTrc97A (European Patent Application EP 0 236 978) was digested with EcoRI and the staggered 5' ends were eliminated with the single strand specific enzyme mung bean nuclease, thus giving the sequence: 5' AACAGACCATGG 3'. Subsequently the DNA was digested with HindIII and the 2 889 bp fragment was isolated. This fragment was ligated with the 1165 bp BalI/HindIII fragment of the PP4-X cDNA in that the blunt end produced by BalI of the cDNA reacted with the blunted EcoRI end of the vector. The resulting sequence coding for the N-terminal amino acids of PP4-X are:

```
    1    2    3    4    5    6    7
    Met  Ala  Met  Ala  Thr  Lys  Gly
5' ... AACAGACC ATG GCC ATG GCA ACC AAA GGA ... 3'
```

The resulting 4054 bp expression plasmid pPP4-X is thus capable to allow the sythesis of the mature unfused PP4-X protein in E. coli.

In order to express the PP4-X protein the E. coli K12 strain W3110lacIQ was transformed by pPP4-X DNA in the usual way. Ampicillin-resistant colonies express the expected PP4-X protein after induction. Analysis of cellular expression products after SDS-PAGE and staining of bands with Coomassie blue showed a new band of a position corresponding to a molecular weight of approx. 36 kD. Analysis of control cells which were not transformed with pPP4-X DNA do not show this band. The protein which appears in the W3110lacIQ (pPP4-X)-extracts reacts in a Western Blot experiment specifically with anti-PP4 antisera. In a further experiment the cellular proteins of the bacterial culture were labeled with $^{35}$S-methionin after induction by isopropylthiogalactoside (IPTG) and later analysed by SDS-PAGE followed by autoradiography. Again a prominent protein band of approx. 36 kD showed up. This protein is immunoprecipitated by anti-PP4-X antisera.

b) Expression of PP4-X fusionproteins

In a further experiment a PP4-X fusionprotein with E. coli beta-galactoside was made. For that purpose plasmid p BD2IC2OH (European Patent Application (0 236 978) was digested with SmaI and HindIII, the 3.8 kb fragment was isolated and ligated with the BalI/HindIII fragment of the PP4-X cDNA mentioned under (a). The resulting plasmid pBD2IC2OH-PP4-X expressed in E. coli a fusionprotein of approx. 77 kD which consists of the beta-galactosidase part of approx. 41 kD and of the PP4-X part of 36 kD. This fusionprotein is highly expressed and reacts likewise with anti-PP4-X antisera.

Additionally a PP4-X fusionprotein with bacteriophage MS2 DNA polymerase was made. To that end plasmid pEx31c (K. Strebel et al. (1986), J. Virol. 57, 983-991) was digested with EcoRI and the DNA was made blunt-ended with Klenow-polymerase. Subsequently the DNA was digested with HindIII, the 3.2 kb fragment was isolated and ligated with the above-mentioned BalI/HindIII fragment of the PP4-X cDNA. After induction by temperature shift this protein is likewise highly expressed and reacts also specifically with anti-PP4-X antisera.

Both PP4-X fusionproteins are suitable means to produce and to detect antibodies to PP4-X.

We claim:

1. Isolated PP4-X, which has the amino acid sequence shown in Table 1.

2. A pharmaceutical which contains a protein as claimed in claim 1 and a pharmaceutically acceptable carrier.

3. PP4-X obtained by expression of a DNA sequence coding for PP4-X as shown in Table 1 in bacteria, yeasts or animal cells.

4. An isolated protein having PP4-X activity and containing the amino acid sequence as shown in Table 1, with the proviso that the protein is not PP4.

* * * * *